Figure 1A:
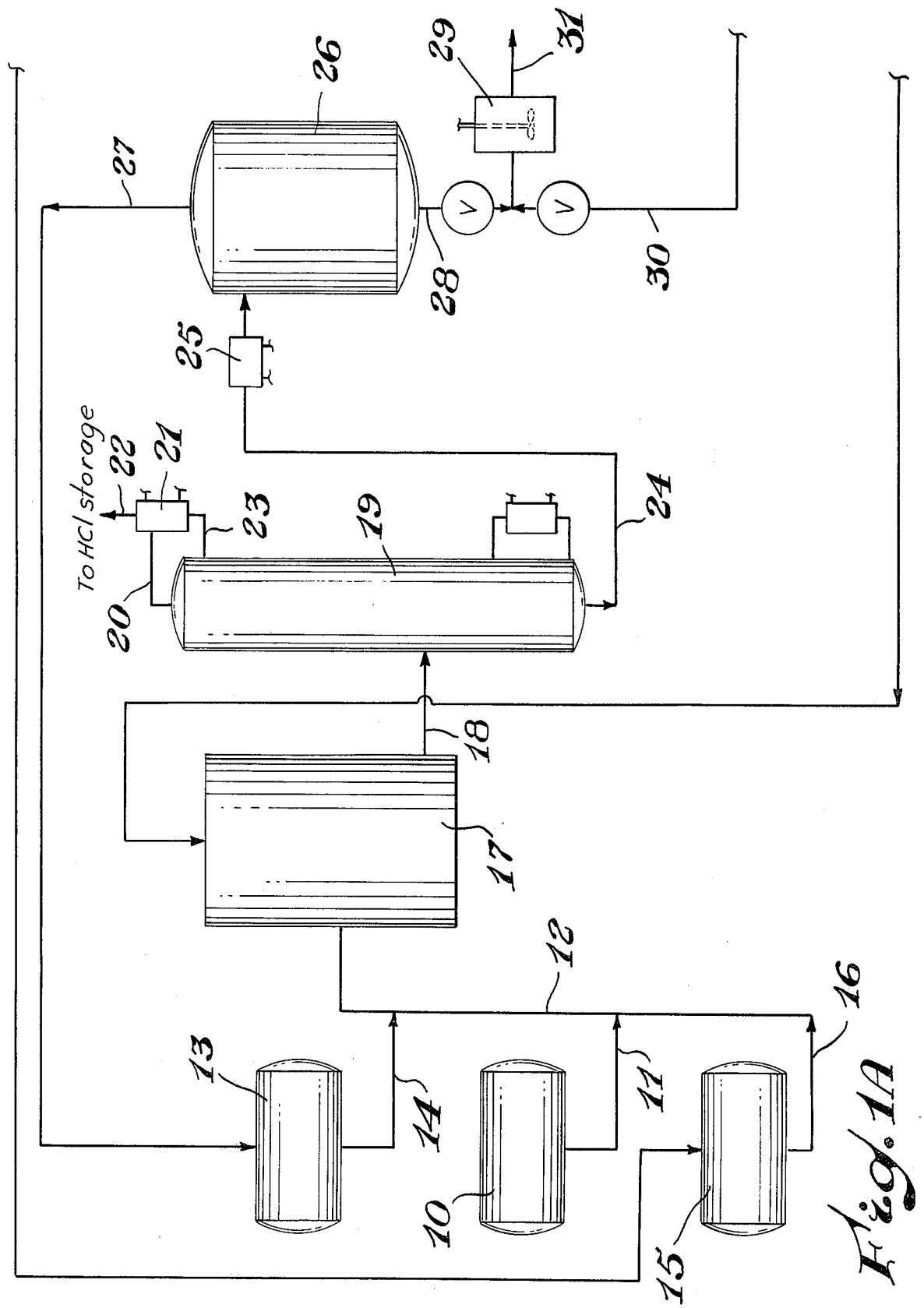
Figure 1B:
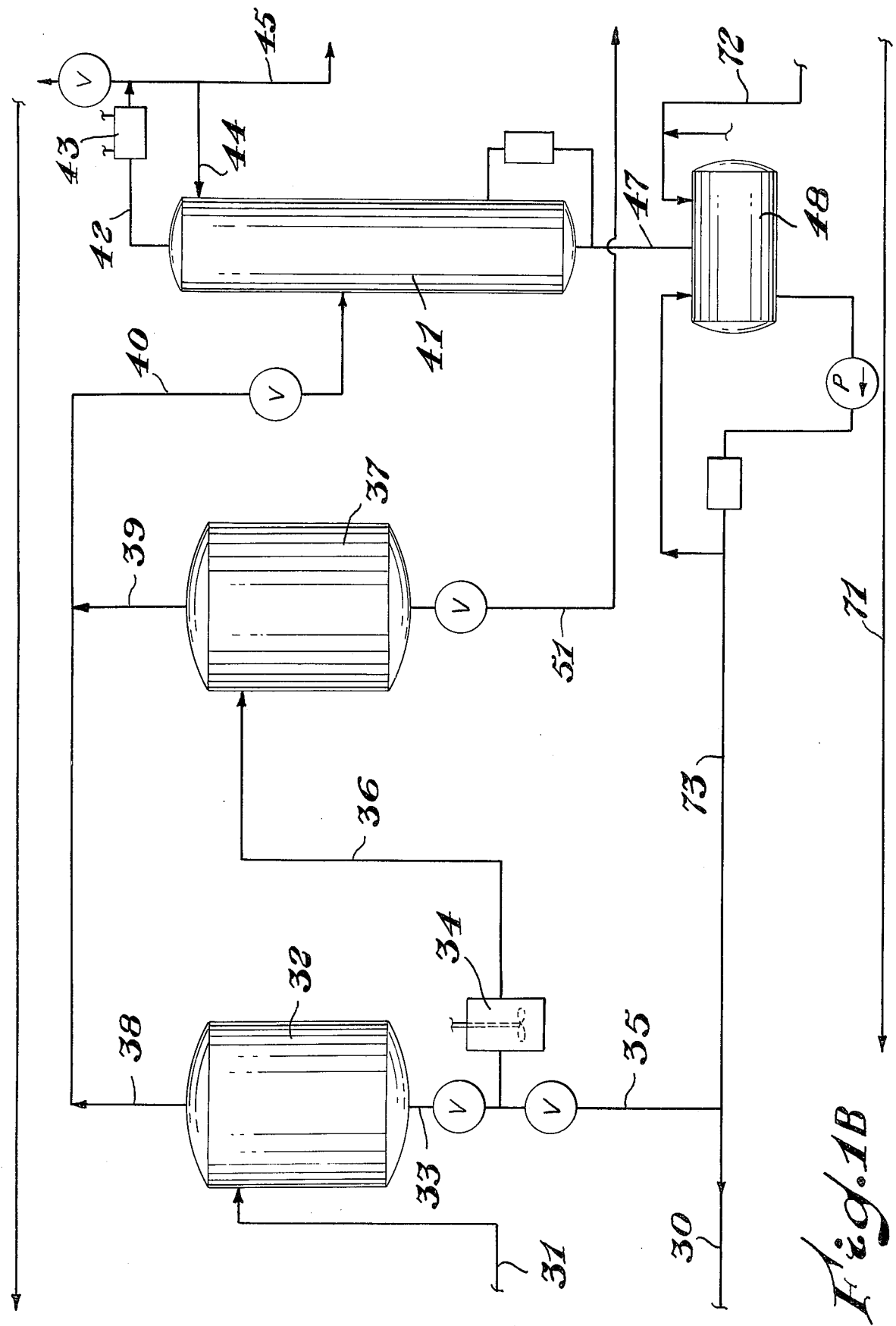

United States Patent [19]

van Eijl

[11] 3,947,558

[45] Mar. 30, 1976

[54] METHOD OF RECOVERING HF FROM MIXTURES CONTAINING $C_1$–$C_3$ HALOCARBON COMPOUNDS

[75] Inventor: A. Theodorus van Eijl, Terneuzen, Netherlands

[73] Assignee: Dow Chemical (Nederland) B.V., Terneuzen, Netherlands

[22] Filed: Aug. 16, 1973

[21] Appl. No.: 389,101

[52] U.S. Cl. ............... 423/483; 203/80; 260/653.7; 423/481; 423/488
[51] Int. Cl.² ......................... C01B 7/22; B01D 3/14
[58] Field of Search ............... 203/80; 260/653.7; 423/483, 484, 481, 488

[56] References Cited
UNITED STATES PATENTS 2,450,414   10/1948   Benning .......................... 203/80 X
2,450,415   10/1948   Benning .......................... 203/80 X
2,478,362   8/1949   Benning ............................. 203/80

FOREIGN PATENTS OR APPLICATIONS 1,271,086   6/1968   Germany ......................... 423/483

Primary Examiner—Leland A. Sebastian
Attorney, Agent, or Firm—Stephen Hoynak; Glwynn R. Baker

[57] ABSTRACT

Hydrogen fluoride can be separated from an organic mixture of fluorinated $C_1$–$C_3$ compounds and recovered for reuse by selectively absorbing the HF in a glycol in which the HF is soluble, but the fluorinated organic compound is substantially insoluble. If desired, HF can be obtained in anhydrous form.

9 Claims, 3 Drawing Figures

METHOD OF RECOVERING HF FROM MIXTURES CONTAINING $C_1$-$C_3$ HALOCARBON COMPOUNDS

BACKGROUND OF THE INVENTION

Fluorinated carbon compounds can be made by reacting HF with a chlorinated hydrocarbon in the presence of any known suitable catalyst, e.g., $SbCl_5$ and $SbCl_3$ or chromium oxide. The final reaction mixture contains fluoro-organic compounds, chlorofluoro-organic compounds, unreacted chloro-organic compounds, HCl and unreacted HF.

Prior separations of the HF from such mixtures involved the formation of an organic and an inorganic layer and separation of the layers. The organic layer still contains an appreciable amount of HF which is removed by scrubbing with water and then neutralizing with an alkali. The prior procedures are described in greater detail in U.S. Pat. Nos. 2,450,414, 2,450,415 and 2,478,362. The processes are both wasteful of HF and have the added disadvantage of creating serious disposal problem of toxic fluorides, since recovery from dilute solution is both difficult and expensive.

SUMMARY OF THE INVENTION

It has now been found that the HF dissolved in a mixed $C_1$-$C_3$ fluorinated stream from which anhydrous HCl is first removed and which has been thereafter cooled and separated to form a layer rich in HF and an organic layer containing dissolved HF, can be selectively recovered by mixing the $C_1$-$C_3$ fluorinated organic layer with a mono-glycol in which the fluorinated organic compounds are substantially insoluble. HF is dissolved selectively and two layers form. The layers are separated, and the HF is removed from the glycol layer, by distillation or by any other means, but preferably by distillation.

The HF, which may contain some water, passes overhead during distillation and the glycol containing, at most, only small amounts of unreacted $C_1$-$C_3$ chlorides and/or fluorinated carbon compounds is recycled for mixing with additional fluorinated $C_1$-$C_3$ organic compounds to repeat the steps described above.

The distilled HF which may contain water, and some $C_1$-$C_3$ organic can be subjected to further treatment, by condensing the overhead to form an HF top layer and a $C_1$-$C_3$ fluorinated organic layer which may also contain small amounts of unreacted chlorinated $C_1$-$C_3$ organic compounds. The aqueous HF layer is separated for recycle to the fluorination step or it can be further treated to form anhydrous HF and an aqueous HF azeotrope. The anhydrous HF is recycled to the fluorination step. The organic layer can be fractionated to remove the fluorinated products and the chlorinated organic compound is recycled to the fluorination step.

By following the above procedure, substantially all the fluorinated organic compounds and substantially all the HF are recovered. No other chemicals are used to absorb and regenerate HF and, since no fluorides are present in the waste streams, a serious pollution problem is avoided, and substantially all of the HF is recovered. No fluorinated or chlorinated carbons are sent to disposal systems.

The drawing is a flow diagram of the process, which can be used for preparing $C_1$-$C_3$ fluorocarbons, or chlorofluorocarbons and recovering HF according to this invention.

Referring to the drawing, a chlorinated $C_1$-$C_3$ aliphatic carbon compound from tank 10 (Fig. 1A) is fed through line 11 to line 12. HF is fed from tank 13 through line 14 to line 12. Optionally, and, preferably, a recycle stream containing primarily chlorinated $C_1$-$C_3$ carbon and small amounts of fluorocarbon and chlorofluorocarbon is fed from tank 15 through line 16 to line 12. The mixture of ingredients is fed into reactor 17.

One gas phase process for producing fluorocarbons uses a Cr/Al oxide catalyst, at 200°–350°C. and a pressure 2–15 Kg/cm². One liquid phase route uses a soluble antimony containing catalyst at about 100°C. and a pressure of about 30 Kg/cm². Preferably, the catalyst is dissolved or dispersed in the $C_1$-$C_3$ chlorinated carbon in tank 10. The reaction pressure and temperature in reactor 17 are controlled to maintain fluorination conditions.

From reactor 17, a stream is fed through line 18 to Column 19. The feed stream in line 18 can be continuous or it can be fed batchwise, if desired. In Column 19, conditions are controlled to separate HCl overhead through line 20 into condenser 21, and through line 22 to storage.

The higher boiling condensate and part of the HCl is returned to Column 19, as reflux, through line 23. The bottoms temperature in Column 19, will vary from about 10° to about 115°C. depending on the composition thereof, including the number of C atoms in the chlorinated carbon undergoing fluorination. Thus, for $C_1$ chlorocarbon the temperature can range from about 50°–70°C. and for $C_2$ chlorocarbon the temperature can range from about 80° to about 115°C. In any event, the temperature should be no greater than and preferably slightly below the boiling point of an HF water azeotrope or the boiling point of the most highly fluorinated fraction, so as to maintain the bottoms fraction in a liquid state under the pressure conditions employed.

The bottoms stream which contains HF, the unreacted chlorinated carbon compound, chlorofluoro compounds and fluorocarbon compounds is fed through line 24 to heat exchanger 25 where it is cooled prior to entry into a decanter 26. In the decanter, two layers are formed. The top layer contains most of the HF, and the small amounts of the halogenated carbons. The bottom layer contains very predominantly the halogenated carbons and some dissolved HF.

The top layer, if it is substantially anhydrous, is recycled to tank 13 through line 27 for reuse in the fluorination reaction. If the HF layer contains an appreciable amount of water, it should be dehydrated by known means prior to feeding into the reactor. The steps delineated to this point are those shown in U.S. Pat. Nos. 2,450,414, 2,450,415, and 2,478,362.

In accordance with this invention, the organic or bottom layer from decanter 26 is fed through valved line 28 to mixer 29. A stream of a glycol is fed to the mixer through valved line 30.

In mixer 29, the bottom or halogenated organic layer is thoroughly mixed with the glycol. Here the HF that is contained in the bottom layer is preferentially dissolved in the glycol, while only small amounts of the halogenated organic compounds are soluble therein, and the amount of glycol dissolved in the halogenated organic phase is less than about 0.1% by weight and usually not greater than about 0.02 to about 0.05%.

After thorough mixing, the liquid from 29 is sent through line 31 to settling tank or decanter 32, (FIG.

1B) where two phases form. The lower halogenated organic phase is shown in the drawing as passing through valved line 33 to a second mixer 34, where it is mixed with additional glycol supplied through valved line 35. From mixer 34, the liquid stream passes through line 36 to a second settling tank or decanter 37. Although two mixing and settling stages are shown in the drawing, it is to be understood that a single such mixing and settling stage can be sufficient, or, in the alternative, three or more such stages can be used.

Figure 1C:
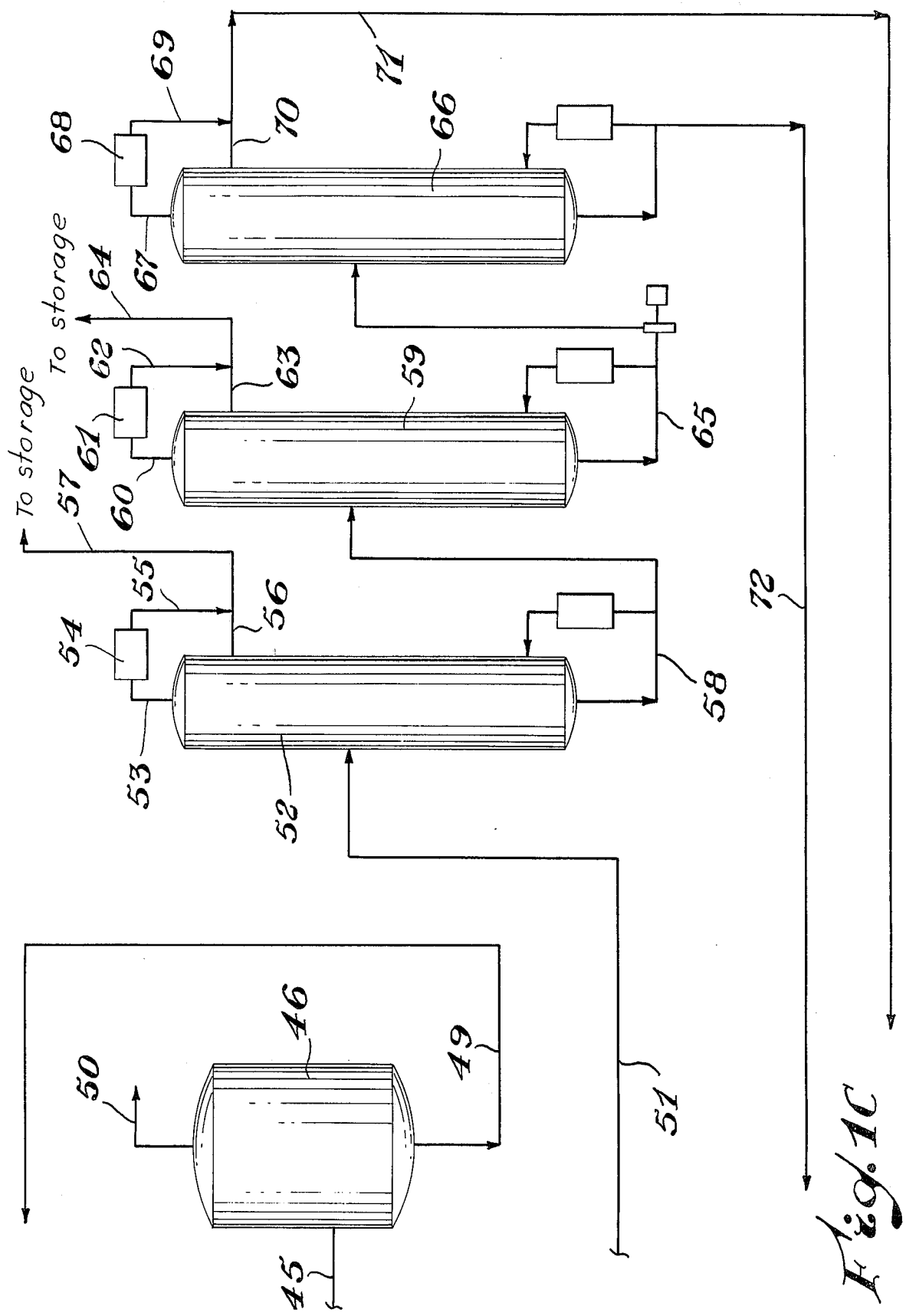

The glycol overhead from tanks 32 and 37 is fed through lines 38, 39 and valved line 40 into a distillation Column 41. In this column the HF and any water which may be present, and the halogenated carbon products are taken off overhead through line 42 and into condenser 43. A portion of the condensate is returned to Column 41 as reflux through line 44 and the remainder is fed through line 45 to a settling tank 46 (FIG. 1C). The bottom product in Column 41 is substantially pure glycol. It passes from the column through line 47 to tank 48 for recycle through line 73. A bottom temperature of from about 150° to about 215°C. is sufficient to strip and purify the glycol in Column 41. It is to be understood that the bottoms temperature in Column 41 can be controlled to remove the specific $C_1$–$C_3$ halogenated carbons being distilled.

In settling tank 46 (FIG. 1C), a top inorganic layer containing HF and any water which may be present in the feed to Column 41 and a bottom halogenated organic layer containing the $C_1$–$C_3$ halogenated carbon compounds are formed. The latter are removed through line 49 and fed to tank 15 for recycle. The inorganic HF rich layer is removed through line 50 and sent to storage or is dehydrated if it contains water, before reuse in the fluorination step. When dry, the HF rich layer can be recycled to tank 13.

The halogenated organic or bottom layer from tank 37 is fed through valved line 51 to Column 52. The feed to the latter column contains fluorocarbon, chlorofluorocarbon and chlorocarbon compounds with small amounts of glycol, usually only 100–300 ppm at 30°C.

In Column 52, the most highly fluorinated compound is removed through line 53, passed to condenser 54, to line 55. A portion of the liquefied product is returned to Column 52 through line 56, as reflux, and the remainder passes through line 57 to storage.

Bottoms from Column 52 pass through line 58 to another Column 59, where compounds of intermediate fluorination are separated overhead through line 60, passed to condenser 61, into line 62. A portion of the liquid is returned to Column 59 through line 63, as reflux, and the remainder is passed through line 64 to storage.

Bottoms from Column 59 contain primarily unreacted chlorocarbon and the glycol which was dissolved in the stream fed to Column 52. The bottoms from Column 59 are fed through line 65 to Column 66, where the unreacted chlorocarbon is removed as overhead vapor through line 67, passed to condenser 68, and the liquefied chlorocarbon is sent to line 69. A portion of the chlorocarbon is returned to Column 66 as reflux through line 70 and the remainder passes through line 71 to the reactor 17. Bottoms from Column 66 are withdrawn through line 72 and returned to the glycol storage tank 48 for reuse in the process.

Representative glycols include ethylene glycol, diethylene glycol, triethylene glycol, tetraethylene glycol, propylene glycol, dipropylene glycol, trimethylene glycol and ditrimethylene glycol. The glycols have from 2 to 8 C atoms. Other glycols which are liquid at the temperature employed in the HF separation steps may also be used. The preferred glycols are ethylene glycol and monopropylene glycol and most preferred is ethylene glycol.

The halogen containing compounds from which HF is separated include the chloro and fluoro $C_1$–$C_3$ compounds and, preferably, they are those obtained in the fluorination of $C_1$–$C_3$ chloro compounds containing an average of at least 2 Cl atoms per carbon atom, e.g., carbon tetrachloride, tetrachloroethylene, and octachloropropane. During the fluorination reaction one or more chlorine atoms on the chlorocarbon is replaced by one or more F atoms.

The fluorinated compounds have known utility as refrigerants or as heat stable heat exchange materials.

EXAMPLE 1

A mixture containing HF, carbon tetrachloride, trichlorofluoromethane, and dichlorodifluoromethane, formed by fluorination of carbon tetrachloride with HF in the presence of $SbCl_5$ and $SbCl_3$ was passed to Column 19, where HCl was distilled from the mixture. The bottoms temperature ranged from 25° to 75°C. The still bottoms were cooled in heat exchanger 25 and passed to decanter 26, where a HF rich layer was separated and passed through line 27 to tank 13 for recycle into reactor 17. The bottom layer from decanter 26 which contains about 1 wt. percent HF was sent to a mixer 29 into which ethylene glycol was fed through line 30. The volume ratio of glycol to still bottoms was 3 to 4. After thorough mixing the ingredients were sent to settling tank or decanter 32, where a top glycol layer containing HF and a bottom layer of halogenated methane were formed. The bottom layer was fed to a second mixer 34, into which additional ethylene glycol was fed through line 35. From mixer 34, the ingredients were fed to settling tank or decanter 37. The top glycol containing layers from decanters 32 and 37 were fed through lines 38 and 39, respectively, to line 40, and into distillation Column 41 where the HF and small amounts of halogenated methane were removed, and then passed into decanter 46 where two layers formed. The layers were separated and sent to recycle. The halogenated carbon layer from decanter or settling tank 37, was fed to distillation Column 52. The ethylene glycol stream contained about 0.5 wt. percent of each of the fluorinated methanes, about 6 wt. percent of carbon tetrachloride and substantially all the HF. Conditions in distillation Columns 52, 59 and 66 are controlled so that the lowest boiling fraction in each still is separated overhead. Thus in still 52, dichlorodifluoromethane was separated, as vapor, condensed and sent to storage. In fractionating Column 59, trichlorofluoromethane is separated and in Column 66 most of the carbon tetrachloride is removed, and recycled to the reactor. The bottoms from Column 66, contains the ethylene glycol which was dissolved in the halogenated carbon stream. The volume is comparatively small and can contain as much as 90 wt. percent carbon tetrachloride and about 10% ethylene glycol. If desired, however, the carbon tetrachloride can be substantially all removed from the glycol. The bottoms stream is returned to glycol storage tank 48 for recycle to mixers 29 and 34, through line 73.

EXAMPLE 2

In this example tetrachloroethylene was fluorinated with HF in the presence of the catalyst described above. The HCl was stripped from the reactor effluent in Column 19. Bottoms from the column were fed to decanter 26, and the top HF rich layer was recycled. The bottom layer, which contained about 1 wt. percent HF, was fed to mixer 29 where it was commingled with ethylene glycol from line 30. The mixture was then fed into settling tank or decanter 32. The top layer of glycol containing HF and small amounts of halogenated $C_2$ compounds was removed through line 38. The bottom layer of halogenated $C_2$ compounds was fed to a second mixer 34, where it was commingled with additional ethylene glycol from line 35. The mixture was then fed to settling tank or decanter 37. The top glycol-containing layer passed through line 39 and combined with that from line 38 and fed to Column 41. The HF and traces of halogenated $C_2$ carbon compounds were distilled and substantially pure glycol was recovered as a bottoms stream which was sent to storage tank 48. The glycol feed to Column 41 contained about 0.3 wt. percent dichlorotetrafluoroethane, about 1.9 wt. percent of trichlorotrifluoroethane and about 2.4 wt. percent of tetrachloroethylene. The overhead Column 41, was condensed and fed to settling tank or decanter 46 where a top HF rich layer and a bottom layer of haloorganic compounds formed. The top layer can be recycled to the reaction, if dry, or dehydrated prior to recycle, if it contains water. The bottom layer was recycled to the fluorination reactor.

The bottom layer from decanter 37 was fed to Column 52, where dichlorotetrafluoroethane was recovered overhead and sent to storage. The bottoms temperature in the column was 175°C. The bottom stream from Column 52 was fed to column 59, where trichlorotrifluoroethane was recovered overhead. Bottoms from this column were fed to Column 66 where tetrachloroethylene was removed overhead and recycled to the fluorination reactor. The bottoms from Column 66 was a mixture of about 90 wt. percent tetrachloroethylene and 10 wt. percent of ethylene glycol. This mixture was returned to the glycol storage tank 48 for reuse. If desired, substantially all the tetrachloroethylene can be removed from the glycol in Column 66 before returning the glycol to tank 48.

When $C_3$ chlorinated compounds are reacted to form fluorinated derivatives, the procedural steps for separating HF from the HF halogenated carbon compound mixture by using glycols is the same as described above, with the exception that temperatures of distillation of the products from the glycol will need adjustment to vaporize and fractionate the specific chlorofluoro compounds undergoing separation.

I claim:

1. A method of recovering the HF which is dissolved in the organic layer obtained after fluorinating a $C_1$–$C_3$ chlorinated hydrocarbon and after separating HCl and cooling to form an HF rich layer and said organic layer, comprising commingling (a) the substantially HCl free organic $C_1$–$C_3$ halocarbon layer containing chloro-, chlorofluoro-, and fluorocarbons with (b) a glycol lean in HF and which is liquid at the temperature employed and which has from 2 to 8 C atoms, forming a glycol layer having hydrogen fluoride selectively dissolved therein and a $C_1$–$C_3$ halocarbon layer containing chloro-, chlorofluoro- and fluorocarbons, separating the $C_1$–$C_3$ halocarbon layer from the glycol layer and recovering hydrogen fluoride from the glycol layer.

2. The method of claim 1 in which the glycol is ethylene glycol.

3. The method of claim 1 in which the glycol is propylene glycol.

4. The method of claim 1 in which step of commingling of the $C_1$–$C_3$ chloro-, chlorofluoro and fluorocarbon layer with a glycol is repeated.

5. The method of claim 1 in which the halocarbon is a mixture of carbon tetrachloride, trichlorofluoro methane and dichlorodifluoromethane.

6. The method of claim 1 in which the halo carbon is a mixture of tetra chloroethylene, trichlorotrifluoroethane and dichlorotetrafluoroethane.

7. The method of claim 1 wherein the lean glycol is recycled and commingled with the said $C_1$–$C_3$ halocarbon.

8. The method of claim 7 in which the glycol is ethylene glycol.

9. The method of claim 7 in which the glycol is propylene glycol.

* * * * *